United States Patent
Spinelli et al.

(10) Patent No.: US 8,604,266 B2
(45) Date of Patent: *Dec. 10, 2013

(54) SHAPE AND PRESSURE ADJUSTABLE DRESSING

(75) Inventors: Thomas Spinelli, Northport, NY (US); Jahangir S. Rastegar, Stony Brook, NY (US)

(73) Assignee: Omnitek Partners LLC, Ronkonkoma, NY (US)

( * ) Notice: Subject to any disclaimer, the term of this patent is extended or adjusted under 35 U.S.C. 154(b) by 317 days.

This patent is subject to a terminal disclaimer.

(21) Appl. No.: 13/046,767

(22) Filed: Mar. 13, 2011

(65) Prior Publication Data

US 2012/0172779 A1 Jul. 5, 2012

Related U.S. Application Data

(63) Continuation-in-part of application No. 12/983,314, filed on Jan. 2, 2011.

(51) Int. Cl.
*A61F 13/00* (2006.01)
*A61L 15/16* (2006.01)
*A61B 17/08* (2006.01)

(52) U.S. Cl.
USPC .............................. 602/53; 424/446; 606/216

(58) Field of Classification Search
USPC ............... 602/41–59; 604/304–308; 424/400, 424/443, 447–449
See application file for complete search history.

(56) References Cited

U.S. PATENT DOCUMENTS

| | | | |
|---|---|---|---|
| 4,605,005 A | 8/1986 | Sheehan | |
| 4,706,661 A | 11/1987 | Barrett | |
| 4,815,468 A | 3/1989 | Annand | |
| 4,865,026 A * | 9/1989 | Barrett | 606/214 |
| 5,630,430 A | 5/1997 | Shultz et al. | |
| 6,306,485 B1 | 10/2001 | Keller | |
| 6,838,589 B2 | 1/2005 | Liedtke et al. | |
| 6,916,967 B2 | 7/2005 | Wright et al. | |
| 7,122,712 B2 | 10/2006 | Lutri et al. | |
| 7,456,332 B2 * | 11/2008 | Beaudry | 602/54 |
| 7,834,232 B2 * | 11/2010 | Rastegar et al. | 606/216 |
| 2003/0150449 A1 | 8/2003 | Spinelli et al. | |
| 2007/0282236 A1 | 12/2007 | LaGreca | |
| 2008/0146982 A1 | 6/2008 | Rastegar et al. | |
| 2008/0167593 A1 | 7/2008 | Fleischmann | |
| 2008/0306456 A1 | 12/2008 | Riesinger | |
| 2010/0318052 A1 | 12/2010 | Ha et al. | |
| 2012/0172778 A1* | 7/2012 | Rastegar et al. | 602/53 |

OTHER PUBLICATIONS

U.S. Office Action Dated Oct. 13, 2009 in related U.S. Appl. No. 11/998,926 (Issued as 7,834,232).

(Continued)

*Primary Examiner* — Patricia Bianco
*Assistant Examiner* — Tarla Patel

(57) ABSTRACT

A dressing for covering a wound. The dressing including: a first component having a first shape; a second component releasably attached to a first surface of the first component to maintain the first component in a second shape different from the first shape; and an adhesive disposed on a surface of the first component different from the first surface for attaching the first component to the wound such that the second component can be released from the first component to allow the first component to take the first shape to apply a pressure to portions of the skin surrounding the wound to close the wound; wherein the second component is a mechanical device.

17 Claims, 12 Drawing Sheets

(56) References Cited

OTHER PUBLICATIONS

U.S. Office Action Dated Jan. 21, 2009 in related U.S. Appl. No. 11/998,926 (Issued as 7,834,232).

International Search Report Dated Dec. 4, 2012 received in corresponding International Application No. PCT/GB2012/052256.
International Search Report Dated Dec. 4, 2012 received in corresponding International Application No. PCT/GB2012/052258.

* cited by examiner

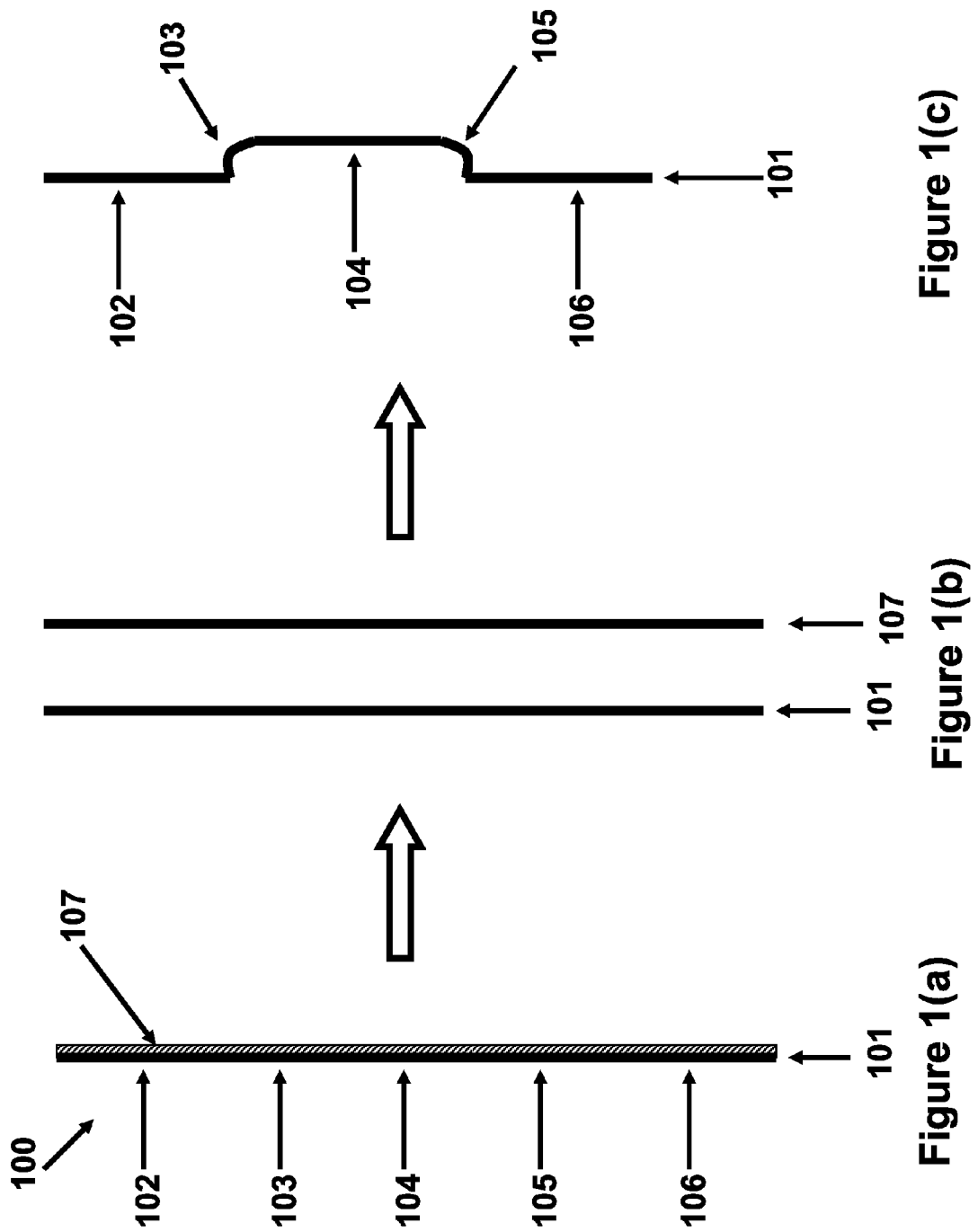

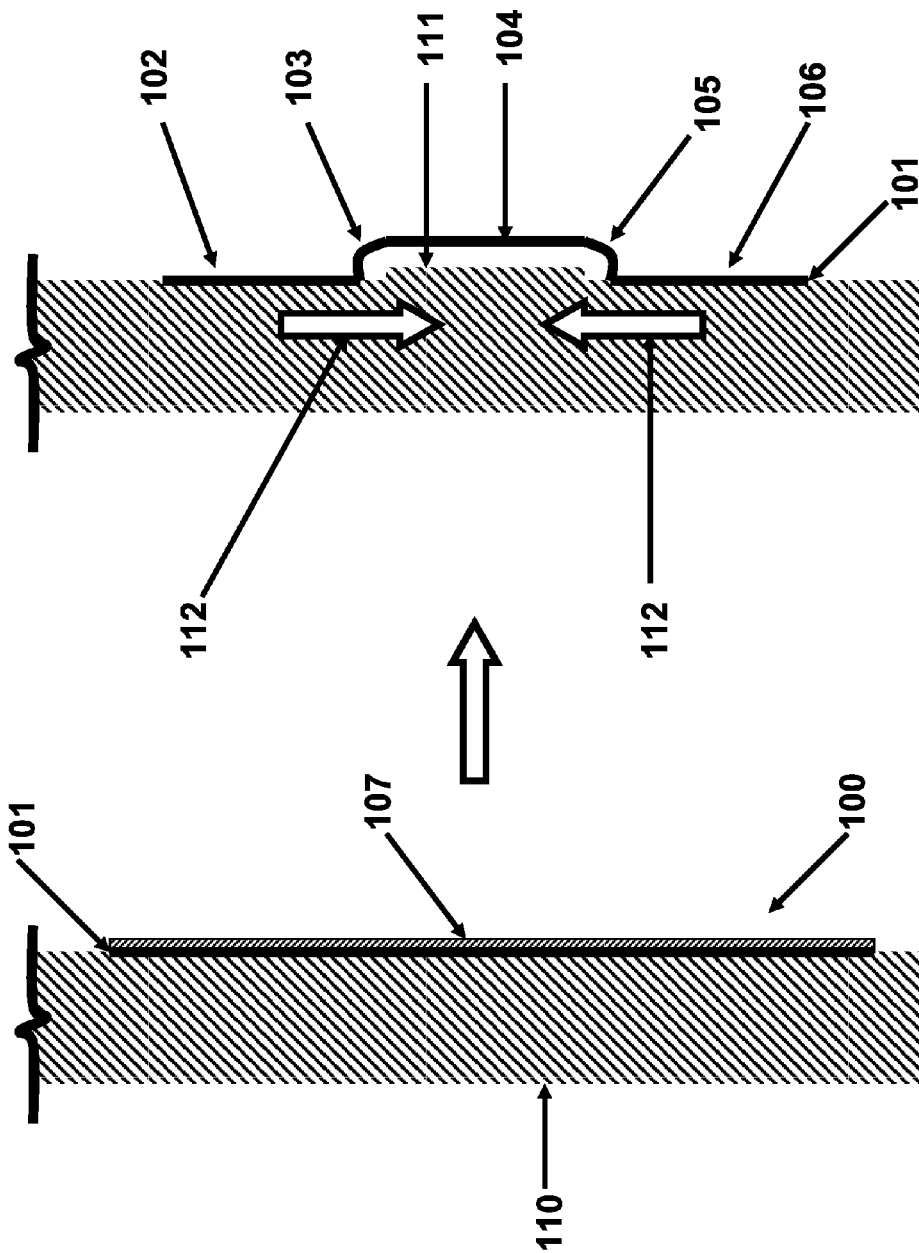

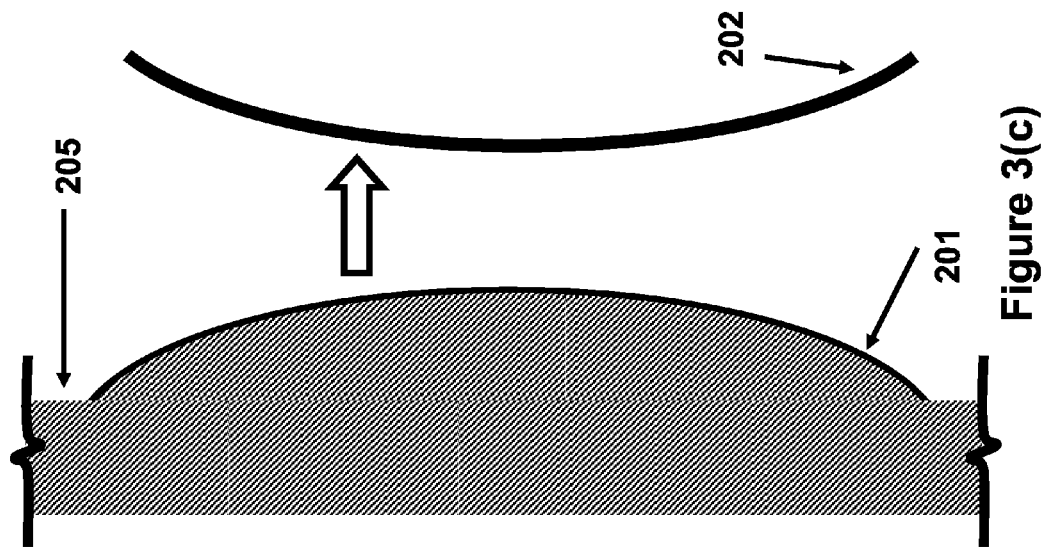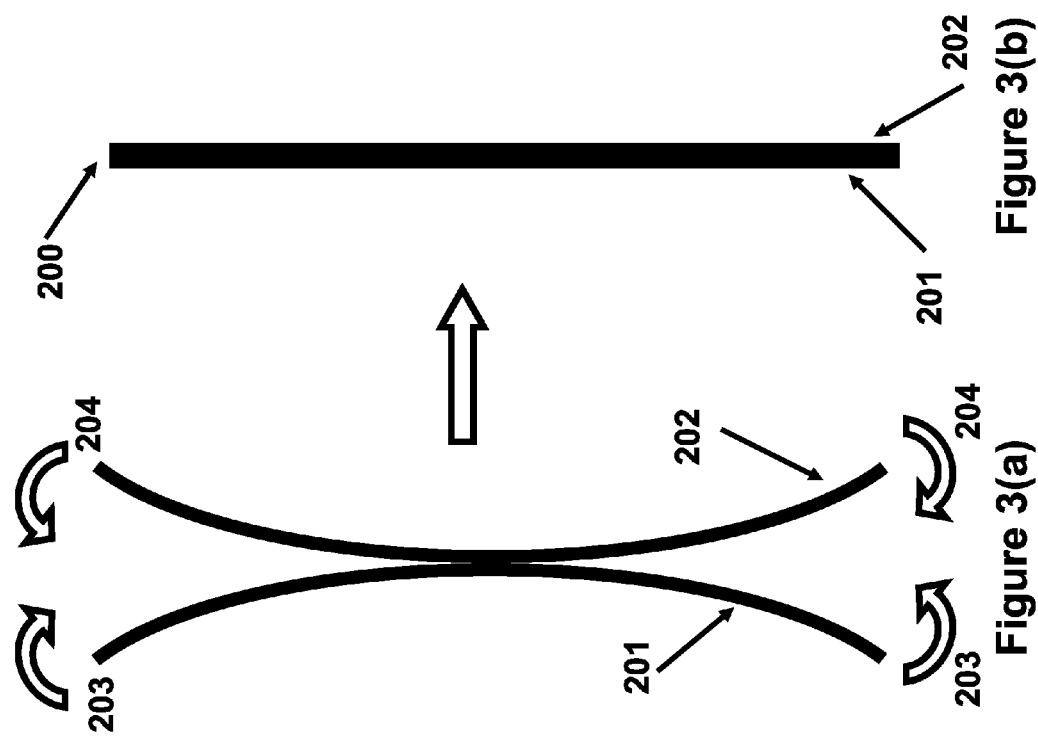

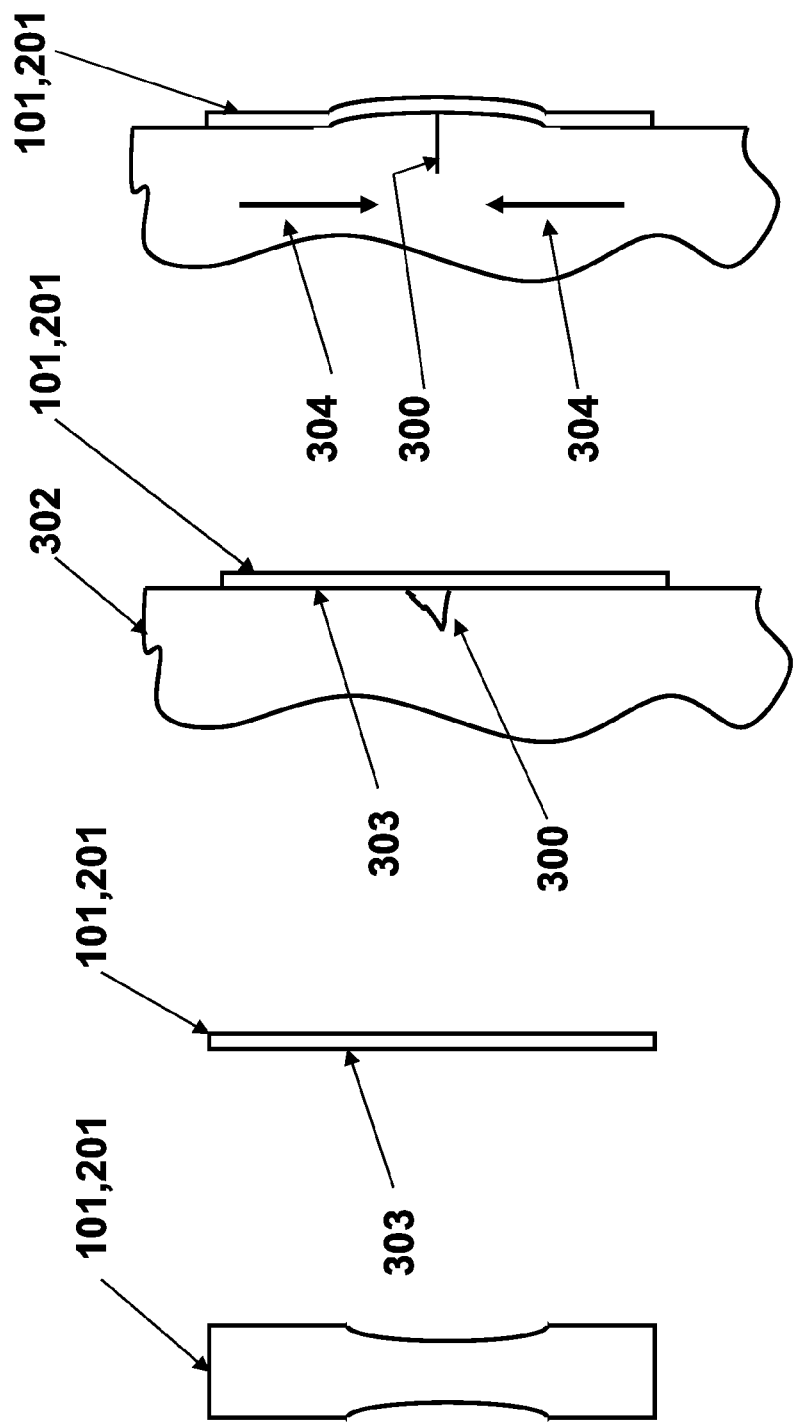

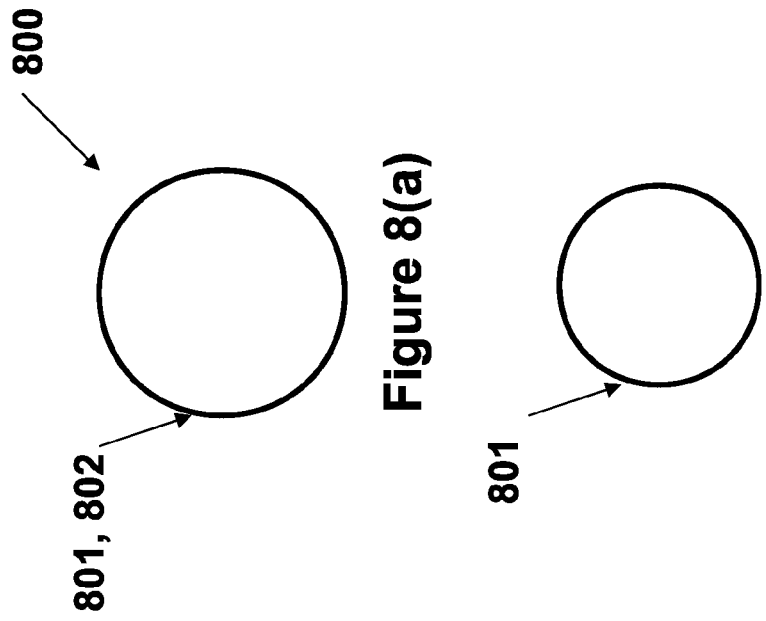
Figure 8(a)
Figure 8(b)
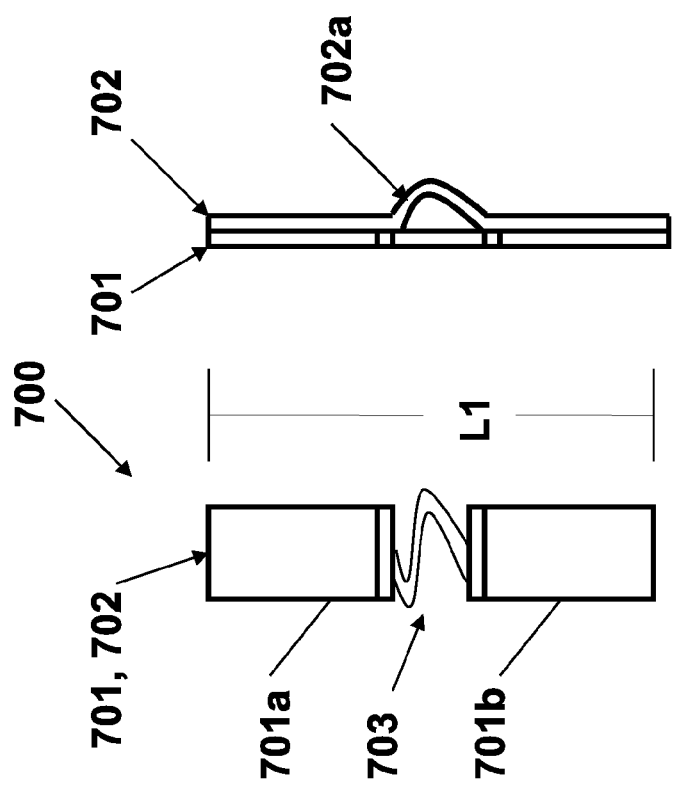
Figure 7(b)
Figure 7(a)

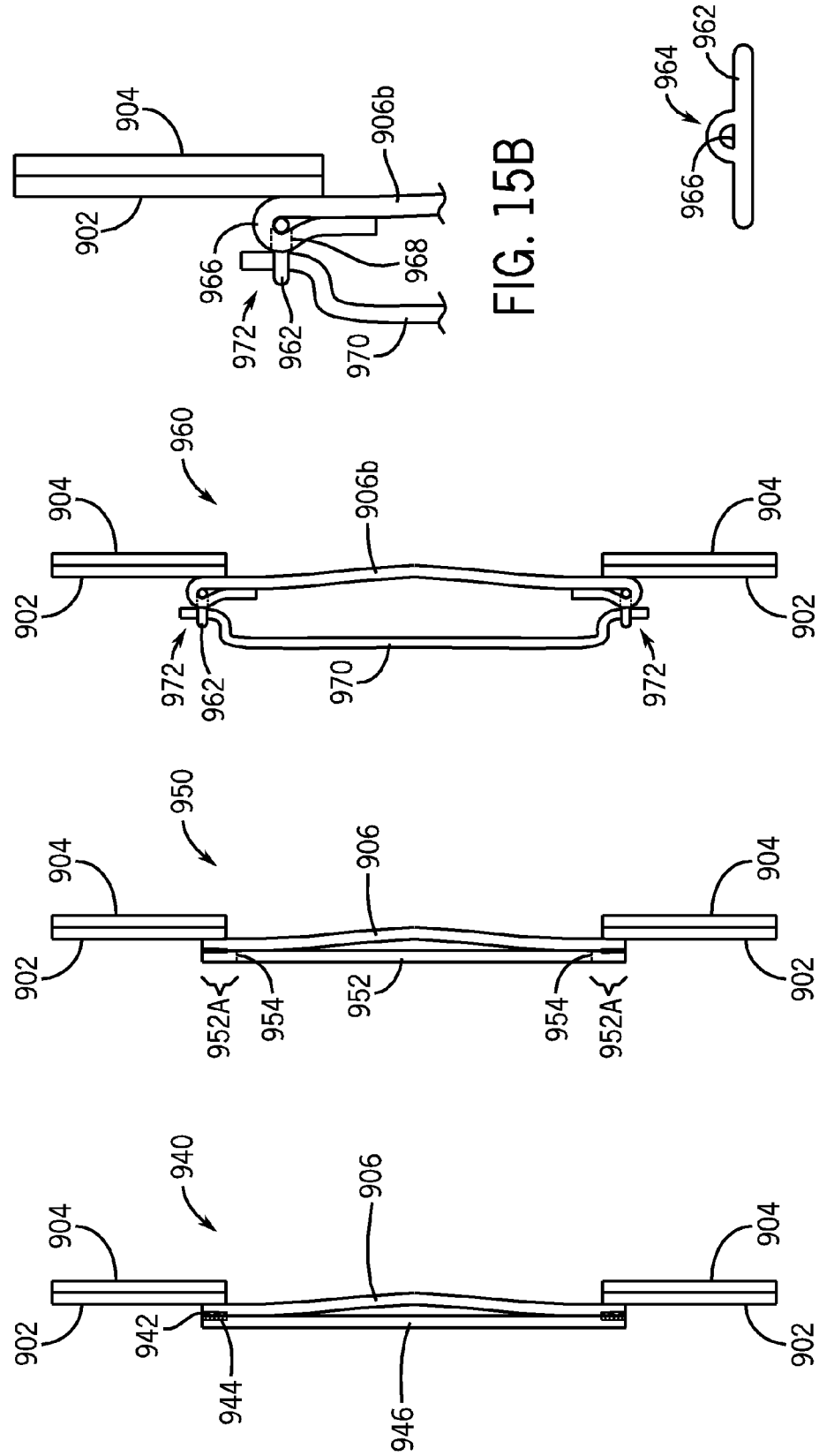

SHAPE AND PRESSURE ADJUSTABLE DRESSING

CROSS-REFERENCE TO RELATED APPLICATION

This application is a continuation-in-part application of U.S. application Ser. No. 12/983,314 filed on Jan. 2, 2011, the contents of which is incorporated herein by reference.

BACKGROUND

1. Field of the Invention

The present invention relates generally to dressings, and more specifically to shape and pressure adjustable dressings.

2. Prior Art

In many situations, dressings are desired to apply a certain amount of pressure on a wound or to apply a certain amount of force to close a wound or keep it closed, even over time as inflammation subsides. In other situations, it may be desired to increase the pressure or force over time to assist healing without a change in the dressing. In yet other situations it may be desirable to vary the pressure or force distribution over time. However, the currently available materials used for dressing wounds are difficult if not impossible to be used to achieve the above results in general, and to achieve it with ease and in a reliable manner in particular, even with the use of such aids as elastic components or tension fixtures.

In other situations, the dressing may be required to cover certain surfaces over the body that due to the shape of the surfaces, it may be difficult to make a close fit and even more difficult to apply pressure to the surface and sustain the applied pressure over time. In such situations, the dressing has to not only conform to the covered surfaces, but at the same time may have to provide a certain pattern of pressure or force to achieve certain goals.

A need therefore exists for a method to construct dressings that can be readily applied to the desired area, and then have the capability of its shape to be varied and/or apply a desired pattern of pressure or force to the covered area. The disclosed methods of varying the shape of the component just before use, is also advantageous in many applications since it can be used to reduce the size of the required packaging, e.g., a blister shaped component may be initially stored as a relatively flat sheet and then be turned to a blister just before application to the patient's skin.

SUMMARY

It is an object of the present invention to provide methods and/or dressings that: a) can be readily applied to a desired area, including areas that are hard to cover due to their shape and geometry; b) can be manipulated to change its shape in a predetermined manner (before or after its application); c) can be made to apply pressure (or a pulling force) to the covered area; and/or d) can be made to apply a force, for example an opening or closing force, in certain direction to the covered area.

Accordingly, a dressing for covering a wound is provided. The dressing comprising: a first component having a first shape; a second component releasably attached to a first surface of the first component to maintain the first component in a second shape different from the first shape; and an adhesive disposed on a surface of the first component different from the first surface for attaching the first component to the wound such that the second component can be released from the first component to allow the first component to take the first shape to apply a pressure to portions of the skin surrounding the wound to close the wound; wherein the second component is a mechanical device.

The first shape can have a first dimension and the second shape can have a second dimension longer than the first dimension. The first and second dimensions can be a length in a single direction.

The change in shape can be due to at least a portion of the first component being formed of an elastic material capable of elastically deforming from the first shape to the second shape.

The first component can include two pockets and the mechanical device can comprise a member having ends disposed in the pockets to maintain the first component in the second shape. The member can include one or more ribs for providing additional resistance to bending. The member can have a variable length. At least a portion of the first component can include one of a hook and loop fastener and the mechanical device can comprise a member in which at least a portion having the other of the hook and loop fastener to maintain the first portion in the second shape.

The mechanical device can comprise a member in which at least a portion is adhered to at least a portion of the first component to maintain the first component in the second shape.

The first component can include two projections each having an opening and the mechanical device can comprise a member having a hook at each end for mating engagement with the openings to maintain the first portion in the second shape.

The mechanical device can comprise a member having a plurality of barbs at each end for grasping at least a portion of the first component to maintain the first portion in the second shape.

The dressing can further comprise a gauze pad disposed on a surface of the first component, the gauze pad including a plurality of gauze strips.

The mechanical device can be a member having one or more weakened portions, wherein destruction of the member about the one or more weakened portions facilitates the change in shape to or towards the first shape.

The mechanical device can be a member having two or more portions and a releasable member for holding the two or more portions together, wherein release of the releasable member partitions the two or more portions apart to facilitate the change in shape to or towards the first shape.

Also provided is a method for applying pressure to skin with a dressing. The method comprising: adhering at least a portion of the dressing to the skin; and subsequent to the adhering, changing the shape of the dressing from a second shape to a first shape by releasing a member from the dressing to allow the dressing to change from the second shape to the first shape such that the changed shape applies pressure to the skin; wherein the releasing comprises one of removing, partitioning or destroying the member used to maintain the dressing in the second shape.

Still further provided is a method for applying pressure to skin with a dressing where the method comprises: adhering a first portion of the dressing to the skin; with the first portion adhered to the skin, changing the shape of the dressing from a second shape to a first shape by application of a force to the dressing to elastically deform the dressing; and with the dressing in the second shape, applying a second portion of the dressing to the skin where the first and second portions bridge a wound on the skin.

The changing step can comprise elongating the dressing from the first shape to the second shape.

BRIEF DESCRIPTION OF THE DRAWINGS

These and other features, aspects, and advantages of the apparatus and methods of the present invention will become better understood with regard to the following description, appended claims, and accompanying drawings where:

FIG. 1(a) illustrates a first embodiment of a dressing having a first layer and a second layer.

FIG. 1(b) illustrates the dressing of FIG. 1(a) in which the first and second layers are separated.

FIG. 1(c) illustrates the first layer of FIG. 1(b) after the second layer has been separated therefrom.

FIG. 2(a) illustrates the dressing of FIG. 1(a) attached to the surface of skin.

FIG. 2(b) illustrates the dressing of FIG. 2(a) after the second layer has been removed.

FIG. 3(a) illustrates two component sheets of a second embodiment of a dressing.

FIG. 3(b) illustrates the two component sheets of FIG. 3(a) attached into an assembly.

FIG. 3(c) illustrates one of the components of FIG. 3(b) attached to the skin of a patient and the other of the components separated therefrom.

FIG. 5(a) illustrates a top view of yet another embodiment of a dressing.

FIG. 5(b) illustrates a side view of the dressing of FIG. 5(a) when at a temperature lower than a threshold temperature.

FIG. 5(c) illustrates the dressing of FIGS. 5(a) and 5(b) attached over a cut in skin.

FIG. 5(d) illustrates the dressing of FIG. 5(c) after the dressing has attained a temperature greater than the threshold temperature to close the cut in the skin.

FIG. 7(a) illustrates a top view of a variation of the embodiment of FIG. 6(a).

FIG. 7(b) illustrates a side view of the embodiment of FIG. 7(a).

FIG. 8(a) illustrates a top view of another variation of the embodiment of FIG. 6(a).

FIG. 8(b) illustrates the dressing of FIGS. 8(a) after the second layer has been removed.

FIG. 13 illustrates yet another embodiment of a dressing.

FIG. 14 illustrates yet another embodiment of a dressing.

FIG. 15A illustrates yet another embodiment of a dressing.

FIG. 15B illustrates a partial enlarged view of the dressing of FIG. 15A.

FIG. 15C illustrates a clip used in the dressing of FIG. 15A.

DETAILED DESCRIPTION

Figure 4C:
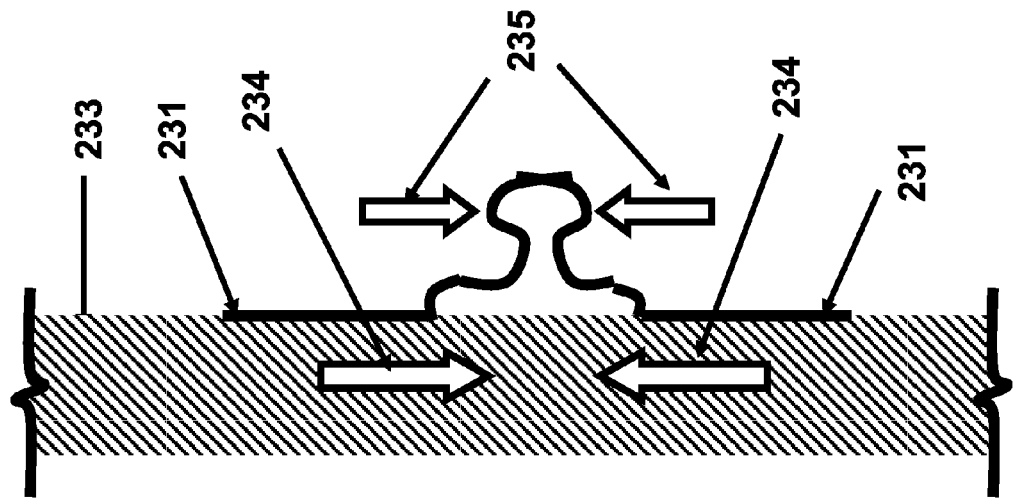
FIG. 4(c) illustrates the dressing of FIG. 4(b) being compressed together.

A schematic of a basic design based on a first embodiment is shown in the FIGS. 1(a) to 1(c). In FIG. 1(a), the cross-section of a plane assembly 100 is shown, and consists of a first layer 101 and a second layer 107. The two layers are attached together using any methods known in the art, such as with adhesives, so that the user could readily separate them. The layer 101 consists of components 102 and 104, which are attached together with an intermediate component 103. Similarly, the components 104 and 106 are attached together with an intermediate component 105. The components 102, 104 and 106 are considered to be relatively devoid of internal stresses, while the components 103 and 105 have been originally shaped as shown in FIG. 1(c), but have been elastically flattened and held in the flattened configuration by the component 107, as shown in FIG. 1 a, to form the assembly 100. Obviously, if the component (layer) 107 is separated from the assembly 100, as shown in FIG. 1(b), the components 103 and 105 would return to their original shape, and the layer 100 will take the shape shown in FIG. 1(c).

The first layer 101 can be formed of any material which can be fabricated into a certain (original) shape and elastically deformed into another shape, such as a plastic or metal or combination thereof. Furthermore, plate 107 can be formed of any material rigid enough to prevent the first layer 101 from taking the original shape while attached to the first layer.

In the schematic of FIGS. 1(a)-1(c), the assembly 100 is shown to be in the shape of a flat plate. It is, however, appreciated by those skilled in the art, that the assembly may form a curved surface; more stressed (preloaded or elastically deformed) and essentially unstressed (preloaded or elastically deformed) components may be used in the assembly; and in their unstressed state, the stressed (preloaded or elastically deformed) component(s) may have been constructed to assume a variety of shapes (configurations), including complex shapes and curvatures. In general, upon the removal of the constraining component(s), the stressed (preloaded or elastically deformed) component(s) will tend to return to their unstressed (natural) state. It is appreciated that the stressed component(s), while tending to return to their unstressed (natural) state (shape or configuration), may still retain part of their induced internal stresses.

The dressing assembly 100 may be applied to the body surface 110, e.g., via an adhesive layer on the free surface of the layer 101 (not shown), as can be seen in FIG. 2(a). Once the assembly 100 is securely attached to the body surface, the layer 107 (wholly or partially) is removed. FIG. 2(b) shows the case in which the layer 107 is removed. At least part of the preloading stresses in the components 103 and 105 are then released. As a result, the layer 101 tends to its natural (stress-free) state. The components 102 and 106 are then pulled towards each other in the direction 112, and the underlying skin is pulled together. Thereby if a cut was present in the section of the skin 111 between the 102 and 106 components, the above action would tend to force it closed. The component 104 of the layer 107 is also pushed away from the skin.

In the schematics of FIGS. 1(a)-1(c), for the sake of simplicity, only two distinct layers are used and only one of the layers is provided with the preloaded components. However, more than one layer can be utilized, and layers with partially preloaded components may also be used to construct the dressing components. It is also possible to construct devices that are constructed with at least two layers of fully preloaded components. In addition, the final assembly (assembly 100) does not have to be flat, and may assume any appropriate shape and configuration as dictated with the particular application.

It should also be noted that in the schematics of FIGS. 1(a)-1(c), and in the remaining illustrations, only living joints are illustrated at discontinuities in the first layer 101. It is, however, appreciated that regular joints, such as pin joints and/or sliding joints, may also be used in the construction of the present devices.

Another embodiment of a dressing is shown schematically in FIGS. 3(a)-3(c). The dressing assembly 200 shown in FIG. 3(b), consists of at least two components (sheets) 201 and 202, which in their free (natural) form are curved as shown in FIG. 3(a). The dressing 200 is assembled by deforming the components 201 and 202 to their assembly configuration and attaching them together, preferably using adhesives, to achieve their final (assembled) configuration. In FIG. 3(a), and for the sake of simplicity, the two components 201 and 202 are shown to be deformed in a symmetrical manner, which upon bending in the directions 203 and 204, respectively, could be nearly flattened to their final shape in the assembly. In this particular case, since the two components 201 and 202 are considered to be identical and with symmetrical initial deformation, then upon their assembly after being flattened would assume a flat configuration. It is readily seen that by using two or more components with varying shape, and/or size, and/or materials, and/or initial (free or natural) configuration, one could construct infinite number of assemblies, which upon partial or full removal of one or more of the components, the desired final shape, size, configuration, and when appropriate applied force (moment or torque) to the attached member, could be achieved.

In certain assemblies, it may be necessary to use less strong adhesives for assembling certain components of the assembly for reasons such as ease of removal. In such cases, it may be necessary to provide mechanical locking action, such as by bending sides or corners of one component over the other, or by using attachment methods such as sewing or stapling or by using one or more clipping elements, etc., which is/are readily removable before applying the dressing to the patient or following its application. FIG. 3(c) illustrates the dressing 200 attached to a surface of the skin and sheet 202 removed, in which case sheet 201 is deformed towards its original shape and the skin takes the shape of the sheet 201 and is pulled together.

Figure 4B:
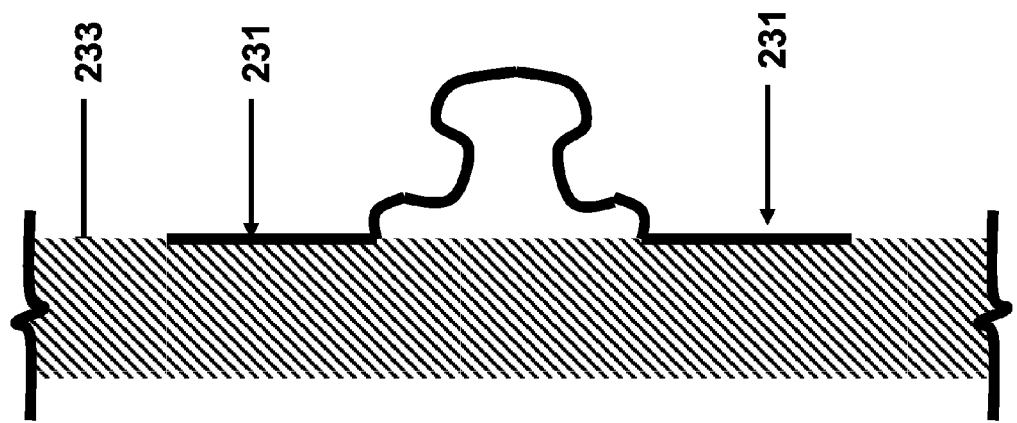
FIG. 4(b) illustrates the dressing of FIG. 4(a) attached to skin of a patient.
Figure 4A:
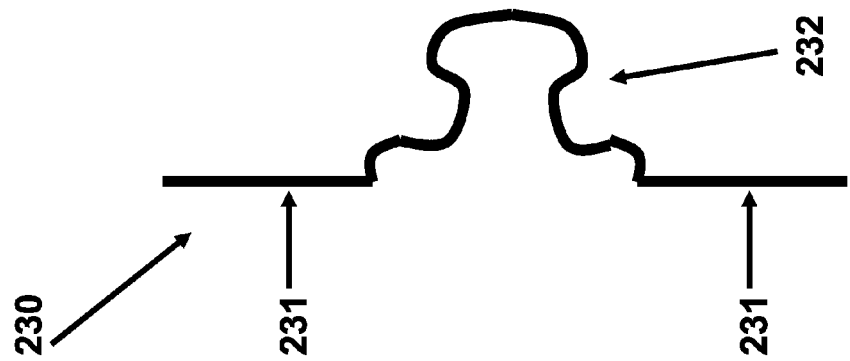
FIG. 4(a) illustrates another embodiment of a dressing.

Yet another embodiment of a dressing is shown in FIGS. 4(a)-4(c). The schematic of the side view of a plate formed with two flat sides 231 and a middle side 232, forming a simple example of a dressing element 230 is shown in FIG. 4(a). The adhesives that are preferably provided on these surfaces may then apply the dressing element 230 to the surface of the skin 233 as shown in FIG. 4(b), via the surfaces 231. The part 232 is then compressed together (or twisted or otherwise deformed) in the direction of bringing the surfaces 231 together (direction 235), such as with a tie-wrap, string wire or the like. As a result, the underlying skin is pulled together in the direction 234, thereby closing a wound or providing a desired compressive pressure, or in short the desired effect.

In all the disclosed embodiments, appropriate dressing components such as gauzes, medications, etc., may be disposed (preferably in the middle regions) of the dressing assemblies to cover the wound. Ventilation or drainage ports may also be provided when appropriate in these regions. Elastic or removable elements may also be provided over or around such regions for administering medication. In certain cases, it may also be desirable to construct one or more components of the assembly with transparent materials so that the affected region could be observed.

In addition, in all the disclosed embodiments, the applied pressure or would closing action of the dressing element may be increased or decreased over time by removing, e.g., a larger piece of the shape/configuration affecting components or by further deformation of the shape/configuration affecting components. You can also vary the pressure applied by the dressing so that the skin can be "pushed" and "pulled."

Referring now to FIGS. 5(a)-5(d), the component 101, 201 disposed on the skin can be formed, at least in part, of a shape memory material. Thus, when disposed on the skin, the component 101, 201 can change shape, in whole or in part, due to a shape memory effect upon being heated by the temperature of the skin to at or above a transition temperature of the shape memory material. Such materials are well known in the art and can be either metals or plastics which exhibit the shape memory effect. A dressing having such a configuration can eliminate the second component 107, 202 since the shape memory material can take one form, such as flat, at a first temperature (FIG. 5(b)) and take another shape, such as that shown in FIG. 5(d) at a second temperature. Thus, the plate 107, 202 is not needed to maintain the sheet 101, 201 in the shape shown in FIGS. 5(a) and 5(b). In this configuration, the dressing component can be shaped as shown in FIG. 5(d) when subjected to a temperature above the threshold temperature (e.g., body temperature) and can be flat when subjected to a temperature lower than the threshold temperature.

This dressing has particular utility when used as a butterfly type dressing for closing wounds that may otherwise require stitches. In this regard, the plan or top view shape of the dressing 101, 201 can be shaped like a conventional butterfly bandage having a narrowed section in the middle thereof, as shown in FIG. 5(a). Once placed over a cut 300 on the skin 302, such as with adhesive on a face 303 of the dressing 101, 201, as shown in FIG. 5(c), preferably disposed on the surface outside of the narrowed portion. After the dressing 101, 201 is warmed by the body heat of the skin, the shape memory material changes its shape to another shape, such as that shown in FIG. 5(d) to close the cut 300 by applying pressure in the direction of arrows 304. The portion of the dressing 101, 201 contacting the cut 300 may have a gauze and/or a medicated layer.

In a variation of such embodiment, the shape memory material dressing can be kept cool and applied to the skin while it is cold. Then the room temperature will activate it to change its shape so that you are not limited to activation with body temperature, which might be very close to the environmental temperature.

Other active materials that could be employed for the dressing could be active polymers, which would require a voltage to get them to pull.

Figures 6A, 6B, 6C:
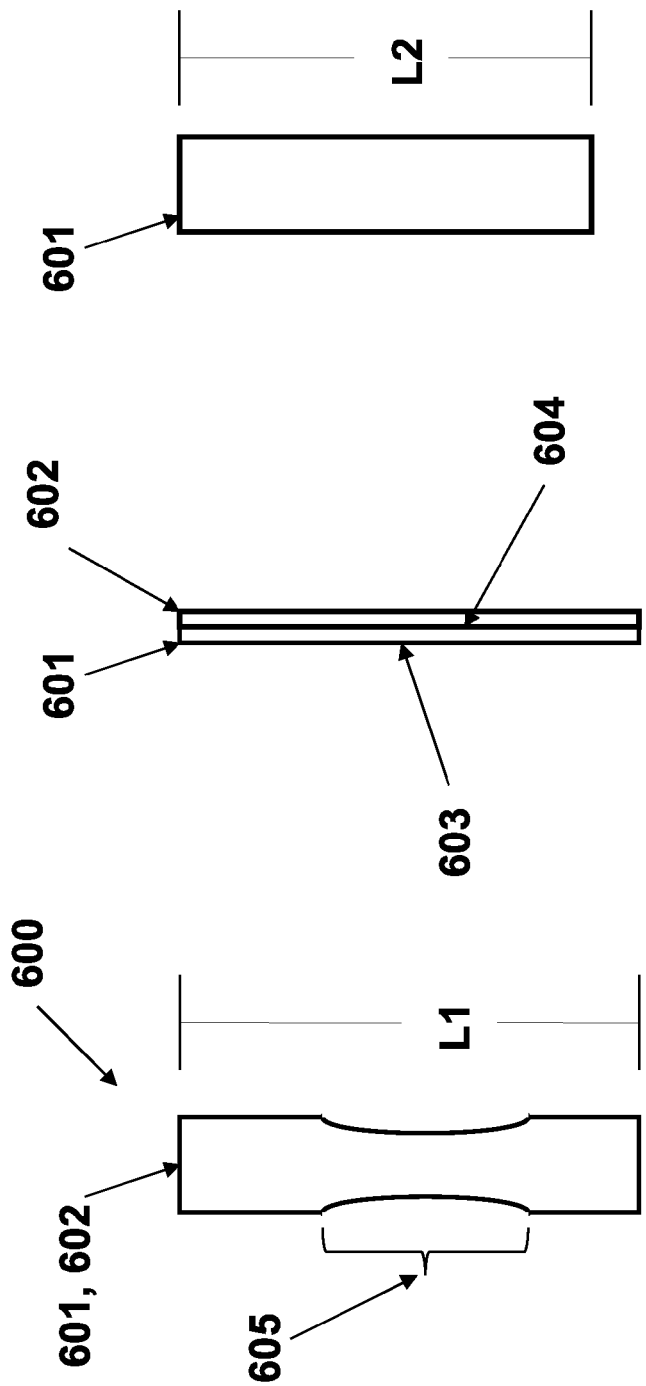
FIG. 6(a) illustrates a top view of yet another embodiment of a dressing.
FIG. 6(b) illustrates a side view of the embodiment of FIG. 6(a).
FIG. 6(c) illustrates the dressing of FIGS. 6(a) and 6(b) after the second layer has been removed.

Another embodiment will now be described in which the shape of the dressing changes after release of a release member, similar to those described with regard to FIGS. 1-4, except that the shape change is a change in length of the dressing. FIG. 6(*a*) illustrates a dressing for a wound, generally referred to by reference numeral 600. The dressing 600 includes a first component 601, which can be a first layer, having a first shape with a first length L1. The dressing 600 further includes a second component, which can be a second layer, which is releasably attached to a first surface 604 of the first component 601 to maintain the first component 601 in a second shape different from the first shape. In the embodiment of FIGS. 6(*a*)-6(*c*), the second shape has a second length L2 which is longer than the first length. An adhesive is disposed on a surface 603 of the first component 601 different from the first surface 604 for attaching the first component 601 to the wound such that the second component 602 can be released from the first component 601 to allow the first component to take the first shape to apply a pressure to portions of the skin surrounding the wound to close the wound.

Thus, the dressing 600 is applied to the skin by adhering the surface 603 to the skin while the first component 601 is constrained into the first shape have a length L1. The second component 601 is then removed from the first component 601 to remove such constraint and allow the first component 601 to take the second shape having a shorter length L2, thus applying pressure to the skin which tends to close a wound.

The first component 601 can be formed of any material which can be fabricated into the first shape and elastically deformed into the second shape, such as an elastic material which can elastically stretch in at least one direction. Furthermore, the second component 602 can be formed of any material rigid enough to prevent the first component 601 from taking the second shape while attached to the first component 601.

In addition to an elastic material, the change of shape from the first length L1 to the second length L2 can be achieved by any other means for elastically biasing the first component 601 into the first length L1, such as one or more elastically deformed members attached at one end to a first portion of the first component and attached at a second (or another end) to a second portion of the first component. An example of such, referred to by reference numeral 700, is illustrated in FIGS. 7(*a*) and 7(*b*) having a biasing member 703 attaching first and second portions 701*a*, 701*b* of the first component 701. Such biasing member 703 can be of any material, such as plastic or metal that can elastically deform into the first shape and back to the second shape. FIG. 7(*b*) illustrates the second component 702 having a loop portion 702*a* adjacent to the biasing member 703 for facilitating removal of the second component.

The first component can have such elastic properties throughout the length L1 or a portion thereof, such as portion 605 which is adjacent to the wound. Also, although the embodiment of FIGS. 6(*a*)-6(*c*) is described with regard to a shape change in one direction, such shape change can occur in a different direction (such as perpendicular to the direction shown) or in more than one direction (such as in the direction shown and a direction perpendicular thereto). An example of such is shown in FIGS. 8(*a*) and 8(*b*), referred to by reference numeral 800, in which the first shape of the first component is a first diameter (shown in FIG. 8(*a*)) and the second shape is a second diameter smaller than the first diameter (shown in FIG. 8(*b*)). Such a variation is useful to apply pressure to the skin in more than one direction to close a wound, such as a puncture wound.

As discussed above, the first component can further include one or more of a medicament and gauze. As also discussed above, the two components can be attached together using any methods known in the art, such as with adhesives, so that the user could readily separate them and more intermediate components (not shown) can be used.

Figure 9B:
FIGS. 9A and 9B illustrate a side view of the dressing of FIG. 9 in a first shape and second shape, respectively, where the second shape is elongated.
Figure 9A:
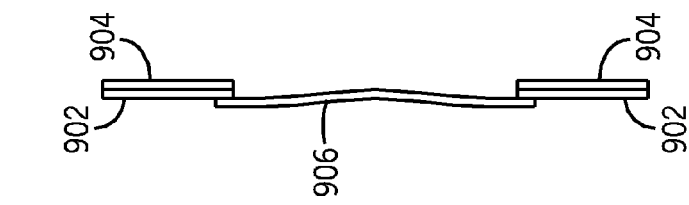

Another embodiment of a shape and/or pressing adjustable dressing will now be described with regard to FIGS. 9, 9A and 9B, referred to generally with reference numeral 900. The dressing 900 includes adhesive portions 902 at each end of the dressing 900 having an adhesive for adhering to skin and a release layer 904 which is releasably adhered to the adhesive portions such that it can be removed when the adhesive portions are to be adhered to the skin. The dressing further includes a portion 906 capable of being elastically deformed from a first shape to a second shape. As discussed above, the change in shape can take a great many forms, such as being elongated, as shown in FIG. 9B (stretched by "S"). In the case where portion 906 changes shape by elongating, the same can facilitate such elongation with biasing elements or elastic material. The adhesive portions 902 and portions 906 can be connected together by sewing, adhering, heat welding and the like. Further, although the adhesive portions 902 and portion 906 are illustrated as separate portions, the same can be integrally formed. As will be described below, the dressing 906, and variations thereof, can be used to close a wound by itself (see FIGS. 18A-18C) or with various holding members, examples of which are described below (see FIGS. 10A-16B). The holding member has been referred to alternatively above as a second component and the adhesive portions 902 and portions 906 as a first component.

Figure 10B:
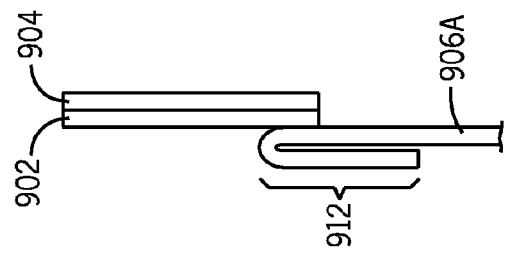
FIG. 10B illustrates a partial section view as taken along line 10B-10B in FIG. 10A.
Figure 10A:
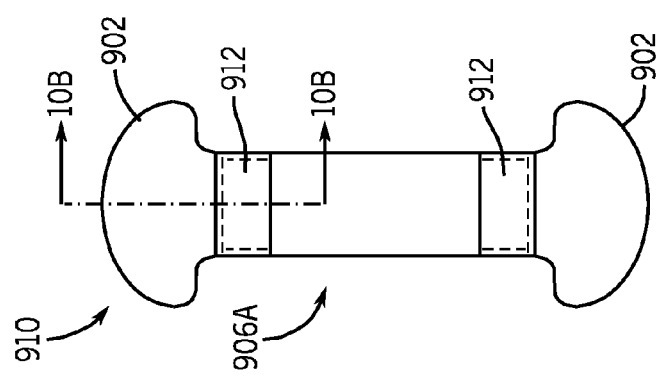
FIG. 10A illustrates a top view of yet another embodiment of a dressing.
Figure 9:
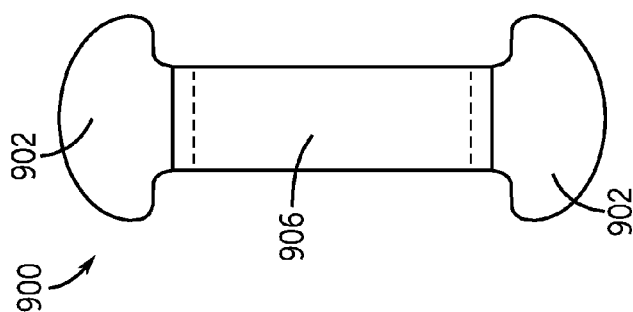
FIG. 9 illustrates a top view of yet another embodiment of a dressing

FIGS. 10A and 10B illustrate a first variation of the dressing 900 of FIG. 9 in which the dressing is used together with a holding member. The dressing, generally referred to by reference numeral 910, is similar to that of the dressing in FIG. 9 in which like reference numerals refer to similar features, except that a pocket 912 is formed at each of two ends of the portion 906A. The pocket 912, as shown in FIG. 10B can be formed by folding over an end of the portion 906A on itself and closing the same to form a pocket 912, by sewing, adhering, heat welding or the like.

Figure 10D:
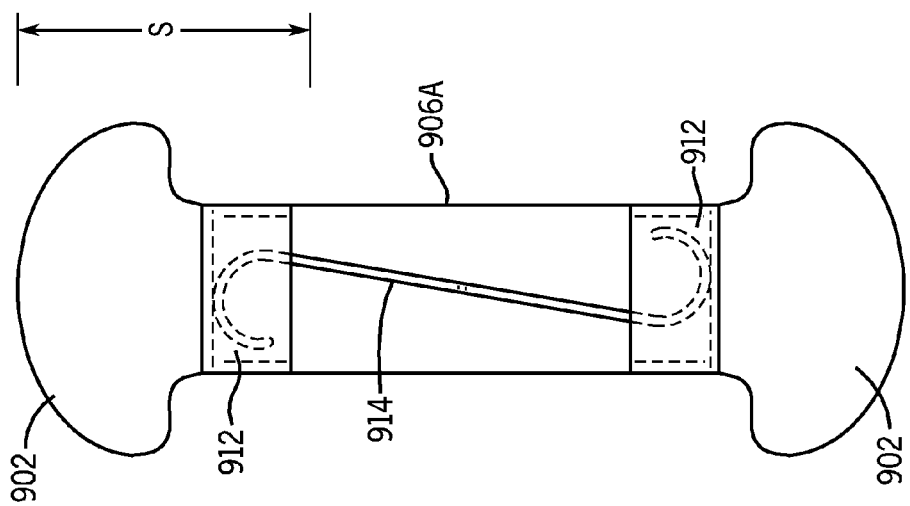
FIG. 10D illustrates a top view of the dressing of FIG. 10A held in an elongated shape with the holding member of FIG. 10C.
Figure 10C:
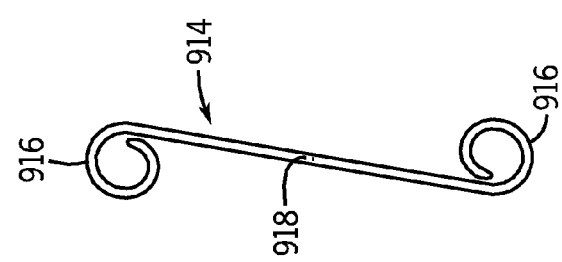
FIG. 10C illustrates a holding member for use in the dressing of FIG. 10A.

FIG. 10C illustrates a holding member 914 which can take any number of shapes, such as having curved ends 916 and a weakened portion 918. The length of the holding member is such that when the curved ends 916 are disposed in the pockets 912, the portion 906A changes shape by elongating a distance "S". The holding member 914 can be formed of many materials, such as wire, plastic and the like as long as it is rigid enough to maintain the portion 906A in the elongated state and may also be flexible such that the holding member and dressing can be applied over a curved surface of the skin. Although shown elongated flat, the holding member can also maintain the portion 906A elongated in a non-linear shape, such as curved.

As discussed above, the dressing 910 can be applied to the skin in the elongated state by removing the release layers 904 and adhering the dressing to the skin about the wound. After application to the skin, the holding member 914 can be removed or released such that the portion 906A can return to or towards its first shape. Such can be achieved by simply removing the holding member 914 from the pockets 912 or cutting or breaking the holding member 914, such as with a weakened portion 918. Such weakened portions are well known in the art and can include a perforated area or reduced cross-section area.

Figure 11:
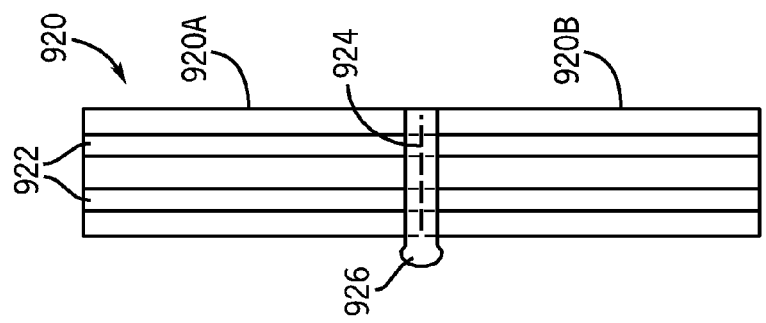
FIG. 11 illustrates an alternative holding member for use with the dressing of FIG. 10A.

As shown in FIG. 11, the holding member can also be a thin member 920 which can have one or more ribs 922 for added rigidity. The thin member can be formed of any material such as plastic. The thin member 920 can be simply removed from the pockets 912 or cut or broken, such as with a weakened portion 924. The weakened portion 924 can be as described above, and may also be realized by forming the thin member of two pieces 920A, 920B and holding the same together with tape 926 or other retaining means. When the dressing is desired to change to or towards its first shape (e.g., un-elongated), the tape is simply removed and the two resulting pieces 920A, 920B of the holding member 920 can be easily removed.

Figure 12:
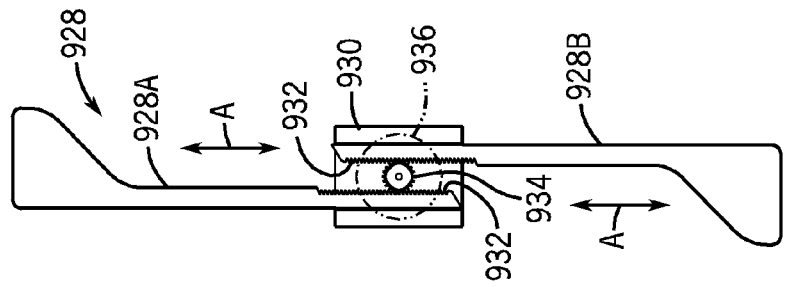
FIG. 12 illustrates another alternative holding member for use with the dressing of FIG. 10A.

FIG. 12 illustrates another example of a holding member 928, in which the length thereof is variable, so as to provide a user of the dressing with a desired elongation depending on the severity of the wound and/or other factors. The holding member 928 includes first and second portions 928A and 928B which are movable relative to each other. For example, the holding member 928 can include a sleeve 930 in which the first and second portions 928A and 928B can move in the direction of arrow A. The first and second portions 928A and 928B can have teeth on an end thereof which mate with a gear 934 which is rotatable on the sleeve 930. Rotation of the gear 934 results in the first and second portions 928A and 928B moving in the direction of arrow A. A knob 936 (shown in dashed lines) can be attached to the gear 930 to facilitate rotation of the gear 930. Thus, with holding member 928, the same dressing and holding member can be used to achieve different amounts of elongation for wounds of different severity.

FIG. 13 illustrates another dressing 940, in which one part of a hook and loop fastener 942 is attached to at least a portion of the adhesive portion 902 or portion 906 and the other part of the hook and loop fastener 944 is attached to at least a portion of a holding member 946. As discussed above, the holding member can be formed of a variety of materials such that it is rigid enough to maintain the portion 906 in the second shape (e.g., elongated) and may or may not be flexible to permit curvature of the dressing 940. When the dressing is desired to change to or towards its first shape (e.g., un-elongated), the hook and loop fastener bond is simply broken by removing the holding member 940.

FIG. 14 illustrates another dressing 950, in which each end portion 952A of a holding member 952 is adhered to a portion of the adhesive portion 902 or portion 906. Such adhesive bond can be removable or permanent. Where the bond is removable, the dressing is changed to or towards its first shape (e.g., un-elongated) by breaking the adhesive bond, i.e., by pulling the holding member 950 away from the portion to which it is adhered. Where the bond is permanent, the holding member can be cut or broken, such as at one or more weakened portions 954.

Referring now to FIGS. 15A, 15B and 15C, there is shown another embodiment of a dressing, referred to by reference numeral 960. The dressing 960 includes a clip 962 having a protrusion 964 with an opening 964. The clip 962 is retained in the portion 906b, such as with a loop 966 of material having an opening 968 for allowing the protrusion to extend from the portion 906b. The clip can be formed of plastic or metal or any material rigid enough for its intended purpose. A holding member 970 is used to maintain the portion 906b in a second shape, such as the portion 906b being elastic and the holding member 970 holding the portion 906b in an elongated state. The holding member 970 has ends 972, such as hooks, for engaging the opening 966 in the protrusion 964 of the clip 962. As discussed above, the dressing 960 is adhered to the skin about the wound by removing the release layers 904 and adhering the adhesive portions 902 to the skin. When the dressing 960 is desired to change to or towards its first shape (e.g., un-elongated), the holding member 970 is removed. Alternatively, the holding member 970 can be destroyed, such as by being cut or breaking the same about one or more weakened portions, as described above.

Figure 16B:
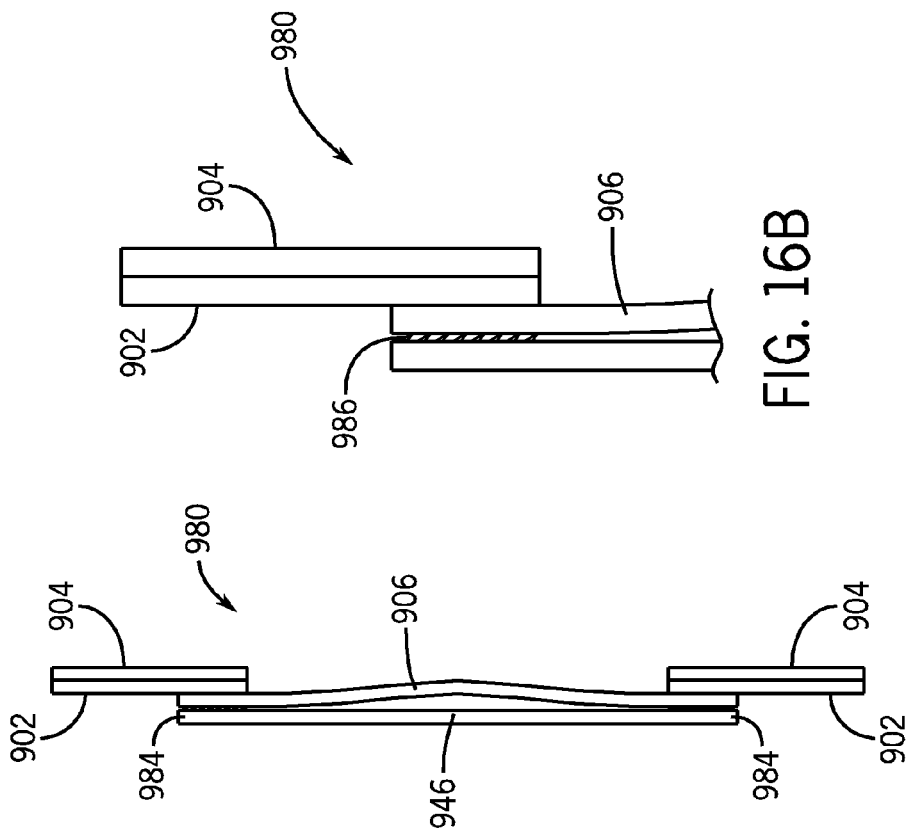
FIG. 16B illustrates a partial enlarged view of the dressing of FIG. 16A.
Figure 16A:
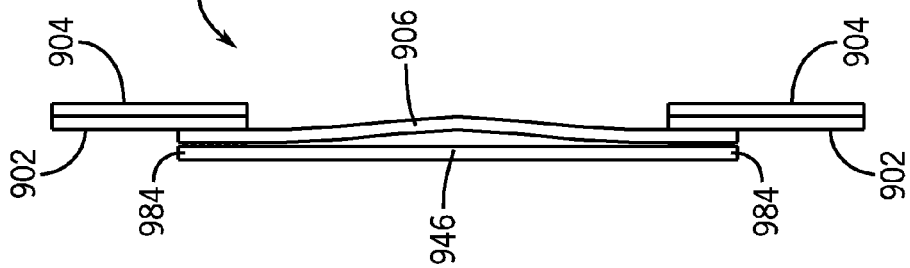
FIG. 16A illustrates yet another embodiment of a dressing.

Referring now to FIGS. 16A and 16B, there is shown yet another embodiment of a dressing, referred to generally by reference numeral 980. The dressing 980 includes a holding member 982 having a surface 984 at each end thereof made of individual barbs 984. The barbs 984 at each can be angled away from each other so as to grab the portion 906 (and/or adhesive portions 904) and maintain the portion 906 in a second shape, such as in an elongated state. The holding member 982 can be formed of a material with sufficient rigidity to maintain the portion 906 in the second (e.g., elongated) shape, such as metal or plastic. After the dressing 980 is adhered to the skin about the wound by removing the release layers 904 and adhering the adhesive portions 902 to the skin, the holding member 982 is removed such that the dressing 960 can change to or towards its first shape (e.g., un-elongated). Alternatively, the holding member 980 can be destroyed, such as by being cut or breaking the same about one or more weakened portions, as described above.

Figure 17B:
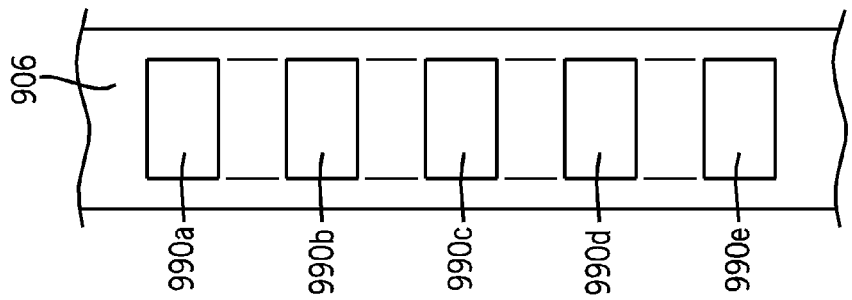
FIGS. 17A and 17B illustrate a variation of a dressing.
Figure 17A:
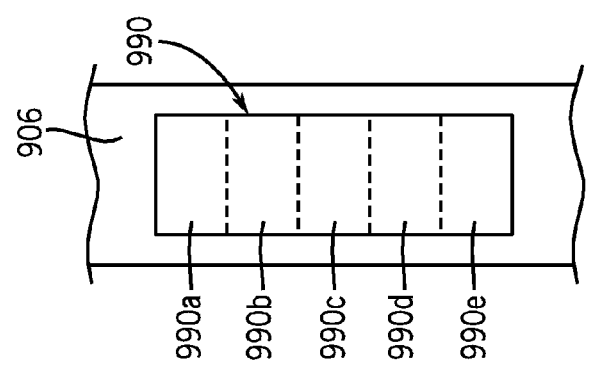

Referring now to FIGS. 17A and 17B, there is shown a variation for use with any of the embodiments described above in which the portion 906 (906a, 906b) changes shape by being elongated. In such variation, the portion 906 includes a gauze pad 990 on a side thereof that contacts the wound. The gauze pad 990 includes strips 990a-990e. Although shown as 5 strips, the gauze pad 990 can be formed of two or more of such strips 990a-990e. The strips 990a-990e are positioned such that they form a continuous (or near continuous) gauze pad 990 when the portion is in its first un-elongated shape. That is, the strips 990a-990e accommodate the elongation of the portion 906 and separate when the portion 906 is elongated.

Figure 18A:
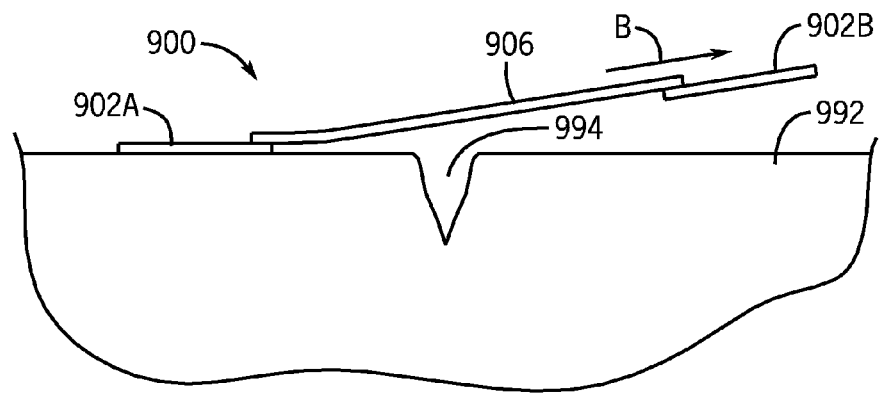
FIGS. 18A-18C illustrate a use of another alternative dressing.
Figure 18B:
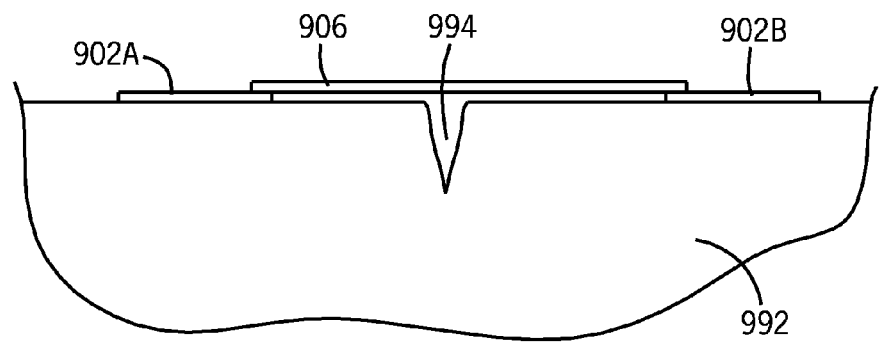
Figure 18C:
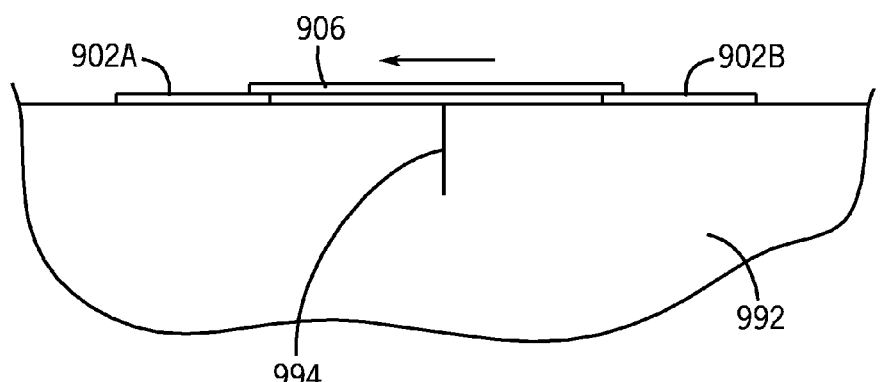

Referring now to FIGS. 18A-18C, the same illustrate an alternative use for the dressings illustrated above. Although applicable to the embodiments described above, the alternative use will be described by way of example with reference to the dressing of FIGS. 9, 9A and 9B. The alternative use for the dressing 900 does not make use of a holding member for maintaining the portion in a second (elongated) shape. As shown in FIG. 18A, one of the release members 904 is removed, exposing the adhesive on the adhesive portion 902A. The adhesive portion 902A is adhered to the skin 992 about a wound 994 to be closed/covered. With the release layer 904 from the other end removed, the dressing is urged into/towards its second shape, such as by pulling in the direction of arrow B and the other adhesive portion 902B is adhered to the skin 992 bridging the wound 994, as shown in FIG. 18B. The dressing 900 then tends to try to return to its first (un-elongated) shape resulting in the wound closing, as shown in FIG. 18C.

Thus, the alternative use described in FIGS. 18A-18C results in the wound closing with time, which, depending on the elastic force in the portion 906 and the severity of the wound, can be from a relatively short time to an extended time. The time delay results in less trauma to the patient because pulling the wound closed tightly at once can be painful. Furthermore, the portion can apply a constant pressure over time even though other variables change, such as a reduction in swelling. In dressings of the prior art, the dressing is pulled taught and applied to close the wound. However, such can be very painful to the patient and may not fully close the wound once swelling subsides.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A dressing for covering a wound, the dressing comprising:
    a first component having a first shape;
    a second component releasably attached to a first surface of the first component to maintain the first component in a second shape different from the first shape; and
    an adhesive disposed on a surface of the first component different from the first surface for attaching the first component to the wound such that the second component can be released from the first component to allow the first component to take the first shape to apply a pressure to portions of the skin surrounding the wound to close the wound;
    wherein the second component is a mechanical device.

2. The dressing of claim 1, wherein the first shape has a first dimension and the second shape has a second dimension longer than the first dimension.

3. The dressing of claim 2, wherein the first and second dimensions are a length in a single direction.

4. The dressing of claim 1, wherein the change in shape is due to at least a portion of the first component being formed of an elastic material capable of elastically deforming from the first shape to the second shape.

5. The dressing of claim 1, wherein the first component includes two pockets and the mechanical device comprises a member having ends disposed in the pockets to maintain the first component in the second shape.

6. The dressing of claim 5, wherein the member includes one or more ribs for providing additional resistance to bending.

7. The dressing of claim 5, wherein the member has a variable length.

8. The dressing of claim 5, wherein at least a portion of the first component includes one of a hook and loop fastener and the mechanical device comprises a member in which at least a portion having the other of the hook and loop fastener to maintain the first portion in the second shape.

9. The dressing of claim 1, wherein the mechanical device comprises a member in which at least a portion is adhered to at least a portion of the first component to maintain the first component in the second shape.

10. The dressing of claim 1, wherein the first component includes two projections each having an opening and the mechanical device comprises a member having a hook at each end for mating engagement with the openings to maintain the first portion in the second shape.

11. The dressing of claim 1, wherein the mechanical device comprises a member having a plurality of barbs at each end for grasping at least a portion of the first component to maintain the first portion in the second shape.

12. The dressing of claim 1, further comprising a gauze pad disposed on a surface of the first component, the gauze pad including a plurality of gauze strips.

13. The dressing of claim 1, wherein the mechanical device is a member having one or more weakened portions, wherein destruction of the member about the one or more weakened portions facilitates the change in shape to or towards the first shape.

14. The dressing of claim 1, wherein the mechanical device is a member having two or more portions and a releasable member for holding the two or more portions together, wherein release of the releasable member partitions the two or more portions apart to facilitate the change in shape to or towards the first shape.

15. A method for applying pressure to skin with a dressing, the method comprising:
    adhering at least a portion of the dressing to the skin; and
    subsequent to the adhering, changing the shape of the dressing from a second shape to a first shape by releasing a member from the dressing to allow the dressing to change from the second shape to the first shape such that the changed shape applies pressure to the skin;
    wherein the releasing comprises one of removing, partitioning or destroying the member used to maintain the dressing in the second shape.

16. A method for applying pressure to skin with a dressing, the method comprising:
    adhering a first portion of the dressing to the skin;
    with the first portion adhered to the skin, changing the shape of the dressing from a second shape to a first shape by application of a force to the dressing to elastically deform the dressing; and
    with the dressing in the second shape, applying a second portion of the dressing to the skin where the first and second portions bridge a wound on the skin.

17. The method of claim 16, wherein the changing step comprises elongating the dressing from the first shape to the second shape.

* * * * *